United States Patent [19]

Wakatake

[11] Patent Number: 5,173,741
[45] Date of Patent: Dec. 22, 1992

[54] AUTOMATIC ANALYZING DEVICE

[75] Inventor: Koichi Wakatake, Tokyo, Japan

[73] Assignee: Kabushiki Kaisha Nittec, Tokyo, Japan

[21] Appl. No.: 610,658

[22] Filed: Nov. 8, 1990

[30] Foreign Application Priority Data

Jul. 20, 1990 [JP] Japan .................. 2-190673

[51] Int. Cl.$^5$ .............................................. G01N 1/10
[52] U.S. Cl. .................... 356/246; 356/244; 356/440; 422/64; 422/104
[58] Field of Search ............... 356/244, 246, 414, 416, 356/410, 440; 422/64, 63, 65, 66, 102, 104, 304

[56] References Cited

U.S. PATENT DOCUMENTS

| | | | |
|---|---|---|---|
| 3,625,485 | 12/1971 | Adler | 356/246 |
| 3,819,271 | 6/1974 | Beug et al. | 356/246 |
| 3,917,455 | 11/1975 | Bak et al. | 356/246 |
| 4,291,986 | 9/1981 | Satou et al. | 356/440 |
| 4,634,576 | 1/1987 | Galle et al. | 356/440 |
| 4,699,766 | 10/1987 | Yamashita | 356/440 |
| 4,785,407 | 11/1988 | Sakagami | 356/246 |
| 4,848,914 | 7/1989 | Shiraishi | 356/440 |

FOREIGN PATENT DOCUMENTS 0186152  11/1982  Japan .................. 356/246

Primary Examiner—Richard A. Rosenberger
Assistant Examiner—Hoa Pham

[57] ABSTRACT

An automatic analyzing device includes an endless belt for holding plural reaction receptacles at a certain interval spacing along a straight carrying line, a belt driving device for carrying the reaction receptacles intermittently, in order, from a sample injecting position to an optical measuring position through a reagent injecting position, and a sample injecting device for injecting a necessary amount of sample at the sample injecting position. A reagent injecting device is placed above the carrying line for injecting a reagent corresponding to a measuring item at the reagent injecting position. An optical measuring device optically measures a property of reacted liquid present in the reaction receptacles.

14 Claims, 7 Drawing Sheets

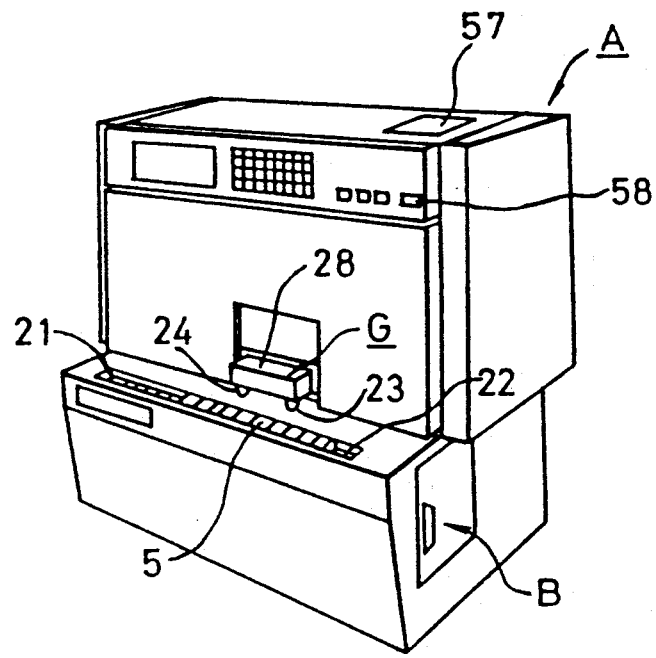
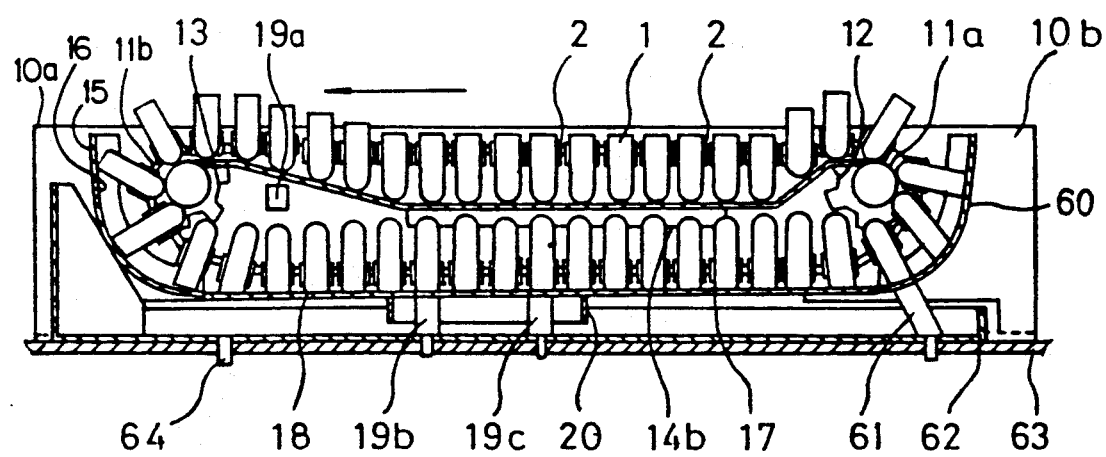
FIG.2

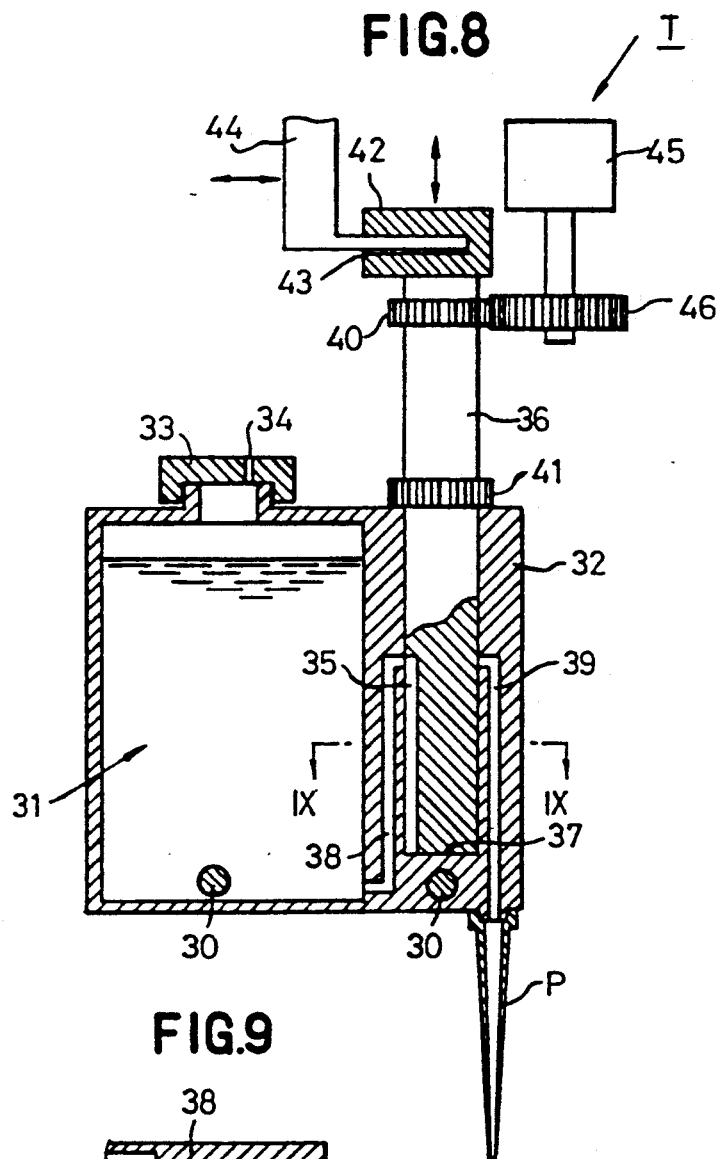
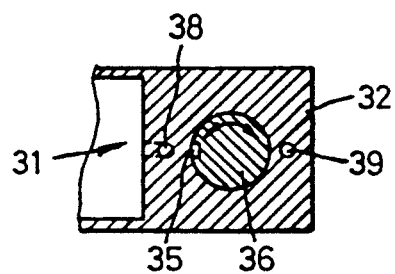

AUTOMATIC ANALYZING DEVICE

FIELD OF THE INVENTION

This invention relates generally to an automatic analyzing device, and more particularly to an ultra-simplified automatic analyzing device for making a biochemical analysis or an immune analysis.

BACKGROUND OF THE INVENTION

Living body fluids, namely, blood, lymph urine, or products produced therefrom, offer useful information concerning the health of a patient, and various kinds of automatic analyzing devices for making a biochemical analysis or a serum analysis of body fluids have been developed.

However, available automatic analyzing devices tend to be complicated, large, expensive, and able to make an analysis speedily, as they are usually designed to carry out many items of test in one automatic analyzing device in a short time.

As a result, small or medium size hospitals such as a local hospital or a private hospital which do not have many tests or not need many items of test have little necessity to have for such large size and high-performance automatic analyzing apparatus, and leave blood tests of their patients to a professional blood test center having a large size and high-performance type automatic analyzing device.

Thus, when an urgent test is necessary in a local hospital or a small or medium size hospital, it takes a long time to obtain the result of an analysis if the blood for the urgent test is carried on all such occasions to a professional blood test center. Test results often do not arrive in time for a surgical operation. Taking the blood to a professional test center furthermore is also uneconomical.

SUMMARY OF THE INVENTION

It is an object of the invention to provide an automatic analyzing device which can make a blood test speedily, without waste, and at a low cost in a local hospital or a small or medium size hospital not having a large number of tests each day.

According to the invention, an automatic analyzing device comprises:
- an endless belt for holding plural reaction receptacles at a certain interval spacing during motion,
- a belt driving device for carrying the reaction receptacles intermittently, in order, along a straight line from a sample injecting position to an optical measuring position through a reagent injecting position,
- a sample injecting device for injecting a necessary amount of sample at the sample injecting position,
- a reagent injecting device placed above the belt for injecting a reagent corresponding to a measuring item at the reagent injecting position, and
- an optical measuring a property of said sample and reagent device for optically measuring reacted in the reaction receptacles.

Other objects and features of this invention will understood from the following description with reference to the accompanying drawings.

BRIEF DESCRIPTION OF THE DRAWINGS

The invention will be described in more detail in conjunction with the following drawings, wherein;

FIG. 1 is a perspective view showing the overall structure of an automatic analyzing device in a preferred embodiment of the invention.

FIG. 2 is a sectional view showing a structure of a belt driving device of the automatic analyzing device.

FIG. 8 is a sectional view showing a structure of a reagent receptacle and a relationship with a piston rod rotation switching device.

FIG. 9 is a sectional view taken along IX—IX line in FIG. 8.

DESCRIPTION OF THE PREFERRED EMBODIMENT

As shown in FIGS. 1 and 2, an automatic analyzing device A in this preferred embodiment comprises an endless belt 2 for holding plural reaction receptacles 1 at a certain interval of spacing. A belt driving device B carries the reaction receptacles along a straight line at a certain timing to an optical measuring position through a sample injecting position, a first reagent injecting position, a second reagent injecting position, and a stirring position. A sample injecting device G injects a necessary amount of sample absorbed from a sample receptacle 5 in the reaction receptacles 1 at the sample injecting position, and a reagent injecting device R injects a necessary amount of a first reagent or a second reagent corresponding to measuring items absorbed from reagent receptacles R1 and R2 in the reaction receptacles 1 at the reagent injecting position See FIGS. 6 and 7. The device A further includes an optical measuring device and a washing device (not shown) for washing the reaction receptacles 1 in which measurement is completed.

Figure 4:
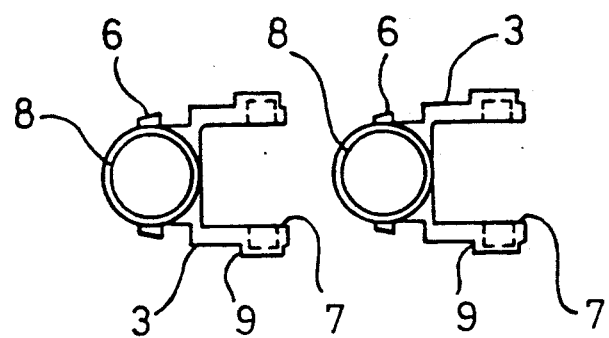
FIG. 4 is a plan view showing an example of a conveyer piece.

As shown in FIG. 4, the endless belt 2 is formed by interconnecting a number of conveyer pieces 3, wherein each conveyer piece 3 has a projection 6, a concave portion 7, a holding hole portion 8, and a convex portion 9.

Accordingly, a belt can be formed by connecting the projection 6 in the conveyer piece 3 to the concave portion 7 in another conveyer piece 3, and as a result, a conveyer having no edge and which has flexibility is formed. The reaction receptacles 1 are set in the holding hole portion 8 in the conveyer piece 3 to slide freely in its axial direction.

Figure 3:
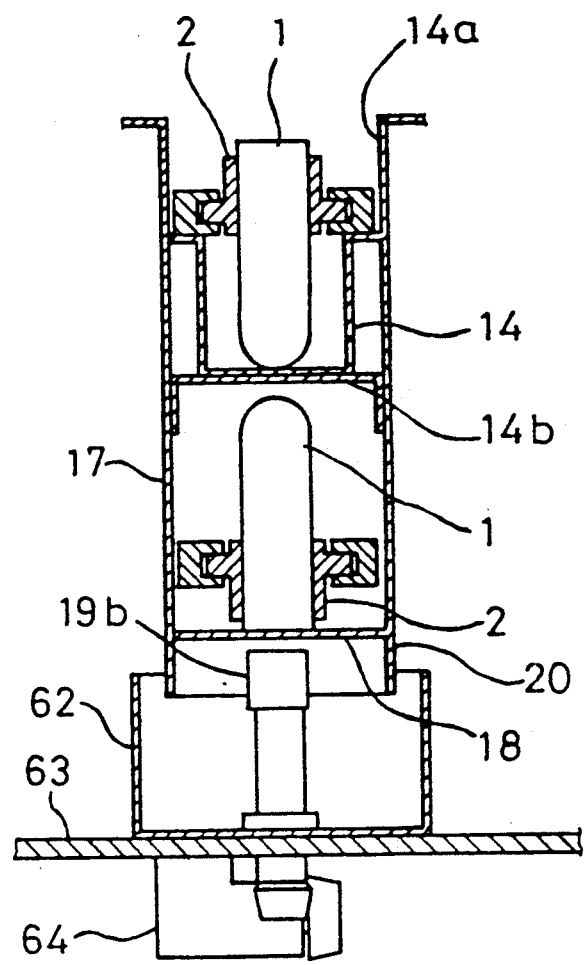
FIG. 3 is a magnified sectional view showing a main portion of the belt driving device.

The belt driving device B for driving the endless belt 2 formed as above is formed as shown in FIG. 2 and FIG. 3.

In the figures, sprockets 12 and 13 are fixed on rollers 11a and 11b held by side boards 10a and 10b, and the sprockets 12, 13 are driven to rotate by a driving device (not shown).

The sprockets 12 and 13 gear into the convex portion 9 in the conveyer piece 3 shown in the FIG. 4, and the endless belt 2 moves intermittently or continuously in the direction of the arrow in FIG. 2 by rotation of the sprockets 12 and 13.

Accordingly, the reaction receptacles 1 held in the holding hole portion 8 in the conveyer piece 3 also move together with the endless belt 2.

The reaction receptacles 1 moving together with the endless belt 2 in this way first reach a thermostat 14. The reaction receptacles 1 reaching the thermostat 14 gradually move down a slope of the thermostat 14. At the lowest position, a serum sample is injected by the sample injecting device G. In this condition, the reaction receptacles 1 are carried to the the first reagent injecting position (not shown) and a second reagent injecting position (not shown). After the first and second reagents corresponding to measuring items are respectively injected at these positions, a reacted sample in the reaction receptacles 1 is measured colorimetrically and optically at a optical measuring position (not shown).

After the optically measuring operation is finished in this way, the reaction receptacles 1 are carried in the direction of the arrow in FIG. 2, reach the roller 11b after moving up a slope of the thermostat 14, and are turned over gradually. A sliding board 15 is positioned to prevent the reaction receptacles 1 from coming off from the endless belt 2 as they turn over.

In the center of the sliding board 15, a narrow groove 16 is made in parallel with the moving direction of the reaction receptacles 1 to minimize an amount of the sample and the reagent flowing in a receiving board 17 by dropping of the sample and the reagent flowing from the reaction receptacles 1 as they are turning over.

The reaction receptacles 1 move, supported by the sliding board 15, and then moves to the receiving board 17 the shape of which resembles the letter "C" and the bottom of which slightly inclines. In the receiving board 17, the narrow groove 16 is made like the sliding board 15 in parallel with the moving direction of the reaction receptacles 1 to minimize an amount of the sample and the reagent flowing in the receiving board 17 by dropping of the sample and the reagent flowing from the reaction receptacles 1 at the time of turning over. The receiving board 17 supports the head of the reaction receptacles 1, similarly to the sliding board 15.

Plural slender long holes 18 are made on the receiving board 17. The long holes 18 are made at right angles to the moving direction of the reaction receptacles 1.

The reaction receptacles 1, carried in this way, are washed when moving on the receiving board 17. In the washing operation, an outside surface of the reaction receptacles 1 is washed by sprinkling washing water from above the reaction receptacles 1 by a washing nozzle 19a fixed on the receiving board See FIG. 2. Inside surfaces of the reaction receptacles 1 are washed by sprinkling washing water from beneath the reaction receptacles 1 by a washing nozzle 19b fixed in a tank 62. Similarly, insides of the reaction receptacles 1 are washed by sprinkling distilled water from beneath the reaction receptacles 1 by a washing nozzle 19c fixed in the tank 62.

The washing water from the washing nozzles 19b and 19c is sprinkled to the reaction receptacles 1 through the long holes 18 made in the receiving board 17, and thereafter flows downward through the long holes 18 again.

A cover 20 is placed under the receiving board 17 to prevent water drops from flying in all directions.

After the above operation is finished, the reaction receptacles 1, carried continuously, reach the second sliding board 60, return in the standing condition gradually, and return to the sample injecting position again. When the reaction receptacles 1 move on the second sliding board 60, a drying operation by hot air is done by a drying nozzle 61 fixed in the tank 62. Water drops on the reaction receptacles 1 fall and any remaining moisture is dried by the hot air.

As shown in FIG. 2 and FIG. 3, under the receiving board 17, the tank 62 is fixed on a base 63 in turn fixed on the side boards 10a and 10b, and water drops from above, the sample and the reagent already measured are received in the tank 62.

The liquid received in the tank 62 is drained to a drain tank (not shown) outside the device through a pipe 64.

As shown in FIG. 3, an upper part 14a of the thermostat 14 and the receiving board 17 support the endless belt 2 and also guide the moving direction thereof. A shielding board 14b is fixed under the thermostat 14, and water drops from the washing nozzles 19b and 19c are prevented from flying in the thermostat 14.

Accordingly, the reaction receptacles 1 in this embodiment are carried as follows.

The plural reaction receptacles 1 held by the conveyer piece 3 of the endless belt 2 to move freely to an axis direction are warmed, in order, in the thermostat 14 and at the same time a sample and first and second reagents are injected therein. After a certain time, the colorimetric measurement is done by the optically measuring device. After the remaining liquid is drained by rolling over of the receptacles 1, and the washing and the drying operation are done in the inverted condition thereof, the reaction receptacles 1 return to the sample injecting position in a standing condition. During the entire process of moving, the reaction receptacles 1 are always supported from beneath by the thermostat 14, the sliding board 15, the receiving board 17, and the sliding board 60, and accordingly, the reaction receptacles 1 are prevented from coming off.

Figure 5:
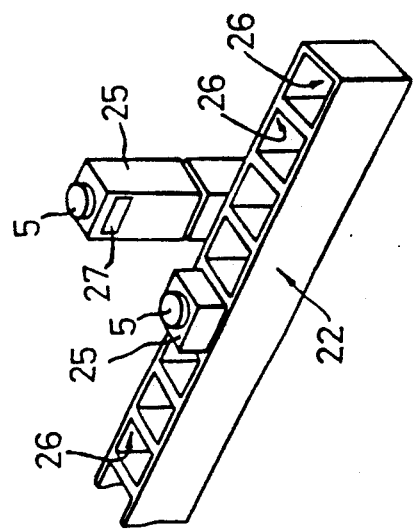
FIG. 5 is a sectional view schematically showing a structure of a sample rack.

The sample injecting device G comprises a sample rack 22 set in a moving groove 21 (see FIG. 1), and a sampling pipette 23 for absorbing a necessary amount of a sample in the sample receptacle 5 is held in the sample rack 22 at the sample absorbing position, as shown in FIG. 5.

As shown in FIG. 5, the sample rack 22 has plural receiving portions in series having an approximately concave shape, in a vertical section, for setting a sample cup holder 25 for holding the sample receptacle 5, and windows 26 on the deep side wall.

Each window 26 is for reading information input in an order mark 27, stuck on the sample cup holder 25, by an optical reading device (not shown).

On the order mark 27, ID information about a sample in the sample receptacle 5 held in the sample cup holder 25, for example, discriminating numbers of patients or sequential numbers of measuring, is adapted to be read optically.

In the sample receptacle 5, a sample for a working curve for amending data as well as a general sample are applied.

The sample rack 22 is made to set the sample receptacle 5 at the sample absorbing position manually or by a conventional driving device.

When a certain sample receptacle 5 is carried to the sample absorbing position in this way, a necessary amount of a sample in the sample receptacle 5 is absorbed by the sampling pipette 23 and injected in the reaction receptacles 1.

The sampling pipette 23 comprises, similarly to a conventional sampling pipette, an arm 28 fixed by an axis 24 at one edge, a pipette 23 placed at the other edge of the arm 28, a sampling pump (not shown) connected to the pipette 23 for absorbing a certain amount of the sample and emitting it in the reaction receptacles 1, and a driving device (not shown) for controlling movement of the arm 28 from the sample absorbing position to the sample injecting position c and to the washing position (not shown) at a certain timing and for controlling rising and falling at each position.

Water is filled in the absorbing means, and after a sample is absorbed and measured in the condition that the sample and the water are separated by air, only the sample is emitted. Thereafter, the pipette 23 is washed from the inside by washing water. At this time, the pipette 23 is set at a pipette washing position, and any sample on the outside of the pipette 23 is washed.

Figure 6:
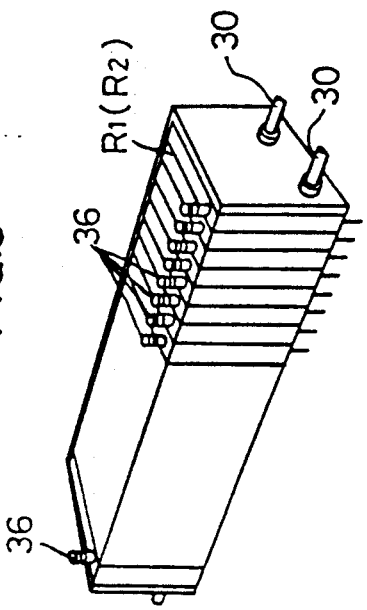
FIG. 6 is a perspective view schematically showing a structure of a reagent injecting device.
Figure 7:
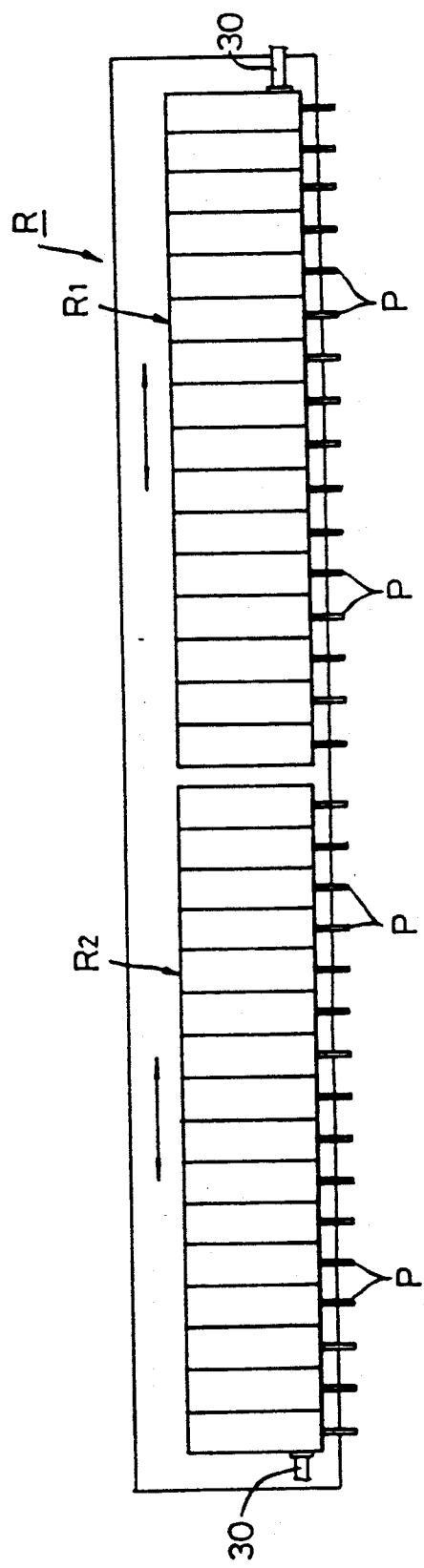
FIG. 7 is a front view showing a reagent injecting device.

As shown in FIG. 6 and FIG. 7, in the reagent injecting device R, a certain number of the first reagent receptacle R1 and the second reagent receptacle R2 are placed in series, right above the moving line of the reaction receptacles 1. Each of the first reagent receptacle R1 and the second reagent receptacle R2 is placed to be able to move in left and right directions in FIG. 7 along a rail 30. A container 31 in which a reagent is received, and a pump 32 for absorbing and injecting a necessary amount of the reagent in the container 31, are incorporated in the reagent receptacles R1 and R2. A liquid injecting entrance is made on the top portion of the container 31 and a removable cap 33 is applied to the liquid injecting entrance. Numeral 34 represents an air hole piercing the cap 33. See FIG. 10.

The pump 32 comprises a valve opening 37 of cylindrical shape having a bottom for retaining freely and tightly a movable piston rod 36 in which one passage groove 35 is cut vertically. A liquid absorbing passage 38 has one edge connected to the valve opening 37 and another edge connected to the container 31. A liquid injecting passage 39 has one edge connected to the valve opening 37 and another edge connected an emitting tube P. By switching to rotate the piston rod 36 every 180 degree angle by piston rod rotation switching device T, as explained below, when the liquid absorbing passage 38 and the passage groove 35 are connected the liquid injecting passage 39 is closed tightly by a surrounding surface 36a of the piston rod 36. When the liquid injecting passage 39 and the passage groove 35 are connected, the liquid absorbing passage 38 is closed tightly by the surrounding surface 36a of the piston rod 36.

The emitting tube P is set at the bottom of the pump 32 to be able to be put on and off, a passage in the emitting tube P and the liquid injecting passage 39 are connected, and the bottom portion of the emitting tube P is set above the reaction receptacles 1 in the moving line.

In this embodiment, the container 31 retains both a reagent received in the first reagent receptacle R1 and the second reagent receptacle R2 and the pump 32 for absorbing and injecting a necessary amount of the reagent. However, the invention is not limited thereto. For example, to reduce maintenance cost of the receptacles when exchanging a reagent and to reduce manufacturing cost, the container and the pump can be made separately so as to enable exchange of the container only.

In this embodiment, the first reagent receptacle R1 and the second reagent receptacle R2 are placed in series on one rail 30. However, the invention is not limited thereto. For example, the first reagent receptacle R1 and the second reagent receptacle R2 can be placed in series on separate rails to be able to move in the moving direction to set more reagents.

The piston rod rotation switching device T is placed right above the reagent injecting position and comprises an upper gear 40 placed at the upper portion of the piston rod 36, a lower gear 41 placed a certain distance below the upper gear 40, and a pressing body 42 placed on the top of the piston rod 36. A piston rod pressing body 44, having an approximate "L" shape, is connected in a connecting groove 43 in the pressing body 42 at a certain position. See FIGS. 10 and 11.

Each of the gears 40 and 41 on the piston rod 36 meshes at a certain position with a gear 46 of a motor 45 when the gear 40 or 41 and gear 46 is in alignment.

The piston rod pressing body 44 rises and falls properly within a stroke by a conventional driving device (not shown). The stroke of the piston rod pressing body 44 depends upon an amount to be injected.

The operation of injecting a certain amount of a reagent from the reagent receptacles R1 and R2, made as above, is as follows.

When the reagent receptacles RI and R2 are carried to each reagent injecting position, the piston rod pressing body 44 is connected to the pressing body 42 on the piston rod 36, as shown in FIG. 8, and thereafter the piston rod 36 is raised. In this case, the gear meshing with the gear 46 of the motor 45 is the lower gear 41. The liquid absorbing passage 38 and the passage groove 35 are connected, the liquid injecting passage 39 is closed tightly by the surrounding surface 36a of the piston rod 36. Accordingly, the first reagent in the container 31 flows in the valve opening 37 through the liquid absorbing passage 38 and the passage groove 35 according to rising of the piston rod 36.

Figure 10:
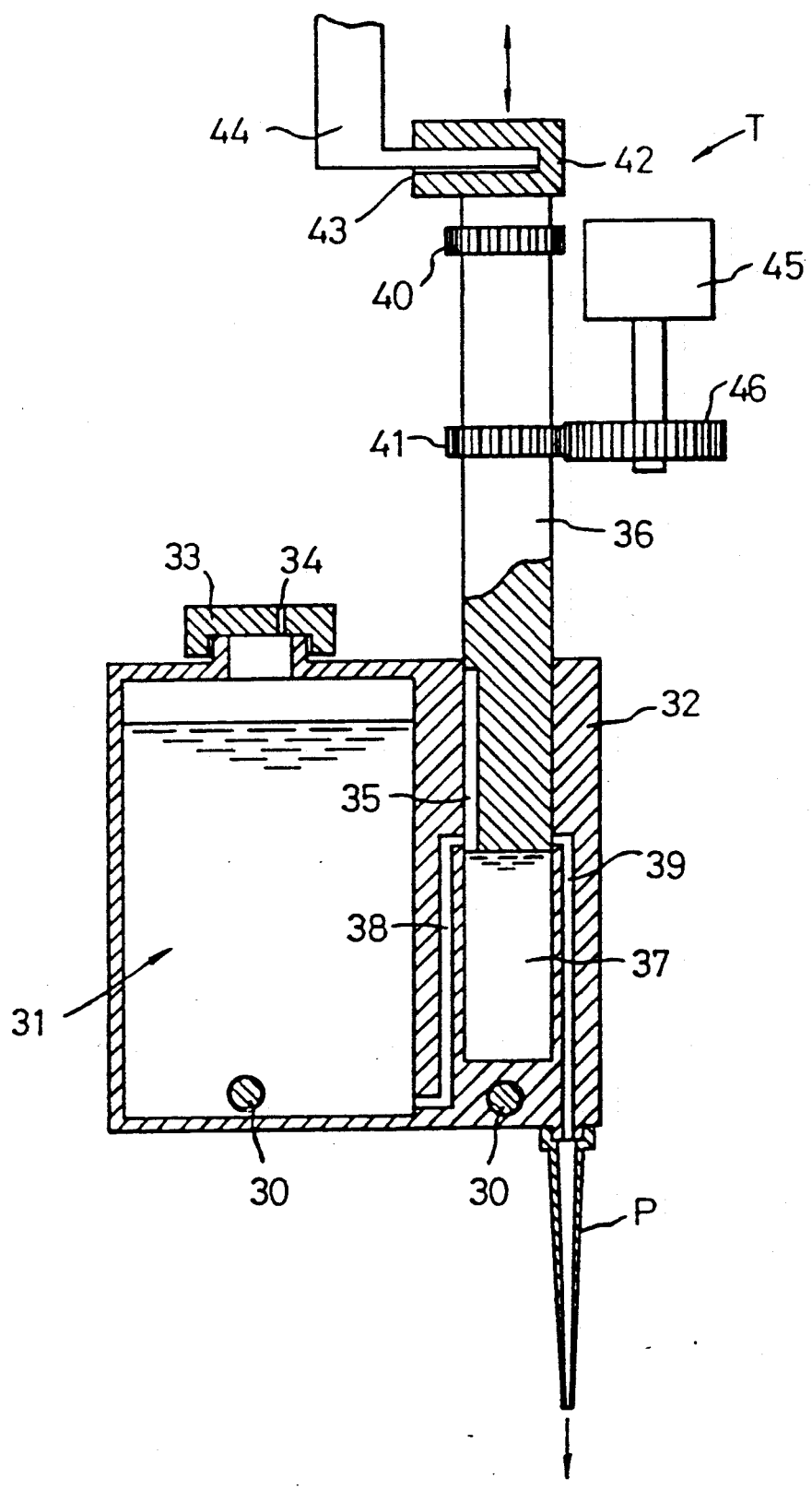
FIG. 10 and FIG. 11 are sectional views showing successive steps of a process for supplying a reagent by a piston rod rotation switching device implemented in the invention.

When the piston rod 36 rises to the position shown in FIG. 10, a certain amount of the reagent is filled in the valve opening 37, and the gear 46 of the motor 45 meshes with the upper gear 40.

Figure 11:
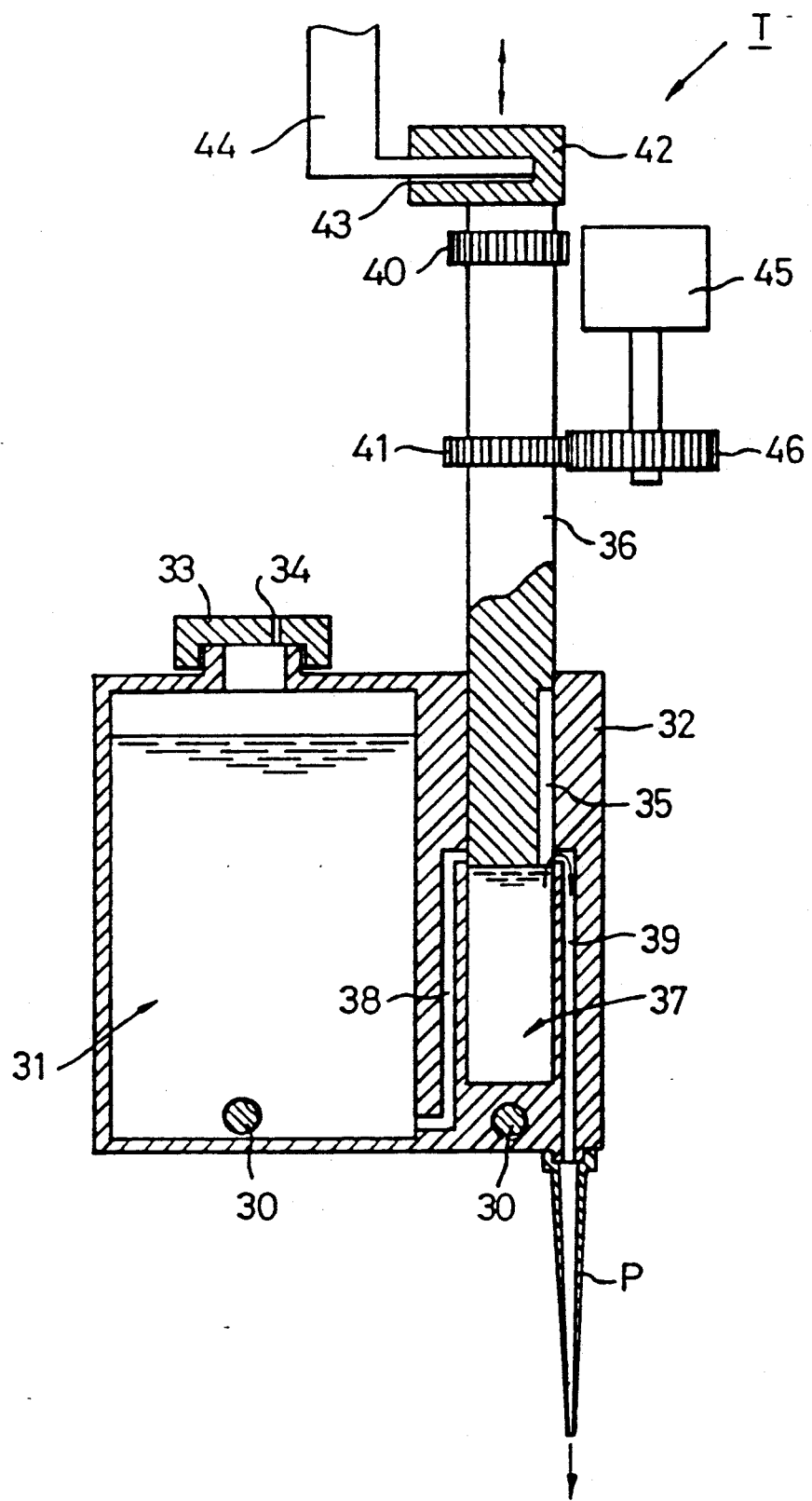

When the piston rod 36 is rotated through a 180 angle by driving the motor 45, as shown in FIG. 11, the liquid injecting passage 39 and the passage groove 35 are connected. The liquid absorbing passage 38 is closed tightly by the surrounding surface 36a of the piston rod 36, and accordingly as the piston rod 36 falls, being pressed by the piston rod pressing body 44, the reagent in the valve opening 37 is injected into the reaction receptacles 1 from the emitting tube P through the passage groove 35 and the liquid injecting passage 39.

After this injecting operation is finished, the upper gear 40 is again controlled to rotate by the gear 46 of the motor 45, and the liquid absorbing passage 38 and the passage groove 35 are set to be connected.

After the reagent injecting operation is finished in this way, the piston rod pressing body 44 and the pressing body 42 on the piston rod 36 are disconnected according to movement of the reagent receptacles R1 and R2. The reagent receptacles R1 and R2 having reagents therein corresponding to the next measuring item are carried to the reagent injecting position, and the reagent injecting operation is done according to the above procedure.

The first and the second reagent receptacles R1 and R2 are previously set at predetermined positions, and their positions are respectively memorized by a CPU. Reagents in the reagent receptacles R1 and R2 are cooled to a temperature of 10°–12° C.

Figure 12:
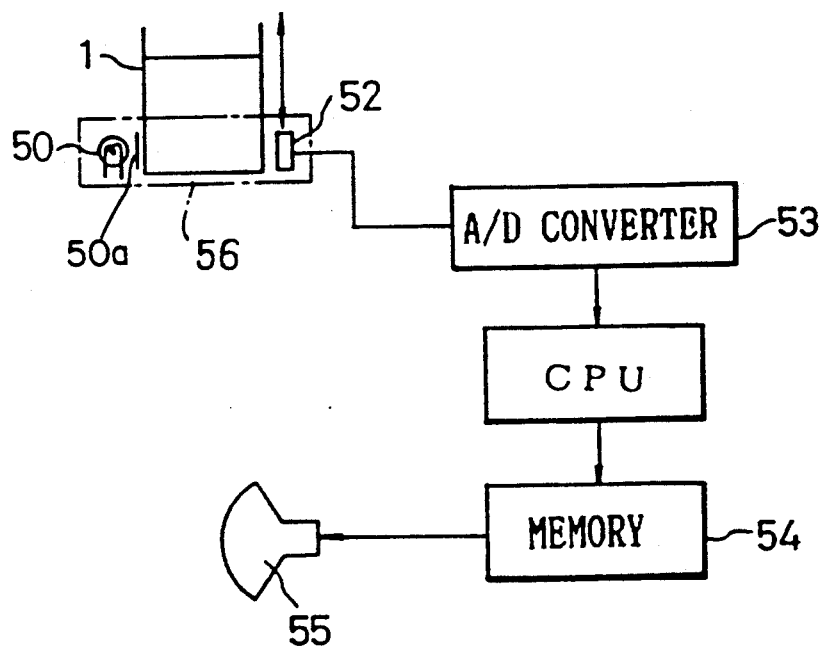
FIG. 12 is a block diagram of an example of a processing circuit for optically measured light as implemented in the invention.

As shown in FIG. 12, the optical measuring device forming a detecting portion at a measuring point comprises a light source 50, a filter 50a for transforming a measuring light irradiated from light source 50 into a wavelength corresponding to a measuring item, and a light receiving sensor 52 for receiving the light at the selected wavelength from the reaction receptacles 1. An A/D converter 53 converts the amount of light received by the light receiving sensor 52 into a voltage. The CPU calculates data figures from the A/D converter 53, and a memory 54 stores the data. The optical measurement device further includes an indicator 55 formed of a CRT etc., a printer 57, and a stabilized power supply/detecting circuit (not shown). A unit 56 accommodates the stabilized power supply/detecting circuit, the light source 50, the filter, and the light receiving sensor 52. A detector moving device (not shown) reciprocates the unit 56 sliding along the moving line of the reaction receptacles 1.

The light source 50 and the light receiving sensor 52 are set at a position through which the moving line of the reaction receptacles 1 passes.

The optical measuring device is placed for the reaction receptacles to cross a light path, and a sample in the reaction receptacles 1 crossing the light path is measured colorimetrically when crossing a light bundle.

It is also possible that by a conventional straight move guiding arrangement, made of ball screw, sliding guide and wire etc. not shown for simplicity, the optical measuring device is reciprocated between the optical measuring position and the first reagent injecting position. The light bundle crosses each reaction receptacle 1 existing therebetween, a cell blank in each reaction receptacles 1 is measured, by the measured figure amending of analyzed data figures is done and reaction time course of each sample is taken. It is also possible that by an absorbing arrangement, reaction liquid is absorbed into a receptacle in a photometer and a degree of absorbed light is measured. A diffraction grating can be applied as the optical measuring device.

The invention is made as above, and the structure of the device can be compact and easy. Accordingly, an automatic analyzing device without trouble can be provided at low cost. Also, and as the reaction receptacles can be re-used by being washed, the operating cost of the test device can be reduced. Accordingly, the automatic analyzing device can meet the needs of a small or medium size hospital e.g., for urgent or night time tests.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. An automatic analyzing device, comprising:
   an endless belt for holding plural reaction receptacles at a certain interval spacing while moving along a carrying line,
   a belt driving device for carrying the reaction receptacles intermittently along a straight line in order from a sample injecting position to an optical measuring position through a reagent injecting position,
   a sample injecting device for injecting a necessary amount of sample at the sample injecting position,
   a reagent injecting device placed above the carrying line for injecting a reagent corresponding to a measuring item at the reagent injecting position, and
   an optical measuring device for optically measuring a property of said sample and reagent reacted in the reaction receptacles,
   wherein said belt passes through a turning over portion, and a sliding board is placed to prevent the reaction receptacles from coming off from the endless belt when the reaction receptacles are carried by the belt over the turning over position.

2. An automatic analyzing device according to claim 1, wherein:
   the endless belt comprises interconnecting conveyer pieces, each conveyer piece having a projection a concave portion, a holding hole portion, and a convex portion.

3. An automatic analyzing device according to claim 1, wherein:
   a narrow groove is provided in the center of the sliding board in parallel with the moving direction of the reaction receptacles to minimize an amount of the sample and the reagent flowing in a receiving board by dropping, at once, the sample and the reagent flowing from the reaction receptacles upon turning over.

4. An automatic analyzing device according to claim 3, wherein:
   a narrow groove is provided in a receiving board contiguous with a trailing end of the sliding board, in parallel with the moving direction of the reaction receptacles to minimize an amount of the sample and the reagent flowing in the receiving board by dropping, at once, the sample and the reagent flowing from the reaction receptacles upon turning over.

5. An automatic analyzing device according to claim 3, wherein:
   a cover is placed under the receiving board.

6. An automatic analyzing device according to claim 3, wherein:
   under the receiving board, a tank is fixed on a base in turn fixed on side boards.

7. An automatic analyzing device according to claim 1, wherein:
   while moving, the reaction receptacles are always supported vertically by a thermostat, the sliding board, the receiving board, and another sliding board.

8. An automatic analyzing device according to claim 1, wherein:
   the sample injecting device comprises a sample rack set in a moving groove, and a sampling pipette for absorbing a necessary amount of a sample in a sample receptacle held in the sample rack at the sample absorbing position.

9. An automatic analyzing device according to claim 1, wherein:
   in the reagent injecting device, a certain number of the first reagent receptacles and second reagent receptacles are placed in series above a moving line of the reaction receptacles.

10. An automatic analyzing device according to claim 9, wherein:
   a container in which a reagent is received and a pump for absorbing and injecting a necessary amount of the reagent into the container are incorporated in the reagent receptacles, a liquid injecting entrance is made on the top portion of the container and a cap is removably applied at the liquid injecting entrance.

11. An automatic analyzing device according to claim 9, wherein
   the first reagent receptacle and the second reagent receptacle are placed in series on separate rails to be able to move in a moving direction of each rail.

12. An automatic analyzing device according to claim 10, wherein:
   the container and the pump are separable.

13. An automatic analyzing device according to claim 1, wherein:
   the optically measuring device comprises a light source, a filter for transforming a measuring light irradiated from the light source into a wavelength corresponding to a measuring item, a light receiving sensor for receiving the light amount after the measuring light having a selected wavelength transmits through the reaction receptacles, an A/D converter for converting the light amount received by the light receiving sensor into a voltage, a CPU for calculating data figures from the A/D converter, a memory for storing data, an indicator including a CRT, and a printer,
   wherein a unit accommodating the light source, the filter, and the light receiving sensor are movably supported to slide along the moving line of the reaction receptacles.

14. An automatic analyzing device according to claim 1, wherein:
   the optical measuring device measures colorimetrically and optically a reacted sample in the reaction receptacles at the optical measuring position.

* * * * *